United States Patent
Lang et al.

(10) Patent No.: US 7,930,028 B2
(45) Date of Patent: Apr. 19, 2011

(54) IMPLANTABLE CARDIAC DEVICE WITH A SHOCK LEAD

(75) Inventors: Volker Lang, West Linn, OR (US); Kurt Swenson, Dayton, OR (US); Jim Nelson, Lake Oswego, OR (US)

(73) Assignee: Biotronik CRM Patent AG, Baar (CH)

( * ) Notice: Subject to any disclaimer, the term of this patent is extended or adjusted under 35 U.S.C. 154(b) by 530 days.

(21) Appl. No.: 11/551,653

(22) Filed: Oct. 20, 2006

(65) Prior Publication Data
US 2008/0097531 A1 Apr. 24, 2008

(51) Int. Cl.
*A61N 1/08* (2006.01)
(52) U.S. Cl. ............ 607/27; 607/6; 607/7; 607/28
(58) Field of Classification Search ......... 607/5, 28, 607/121, 7, 8, 27
See application file for complete search history.

(56) References Cited

U.S. PATENT DOCUMENTS

| | | | |
|---|---|---|---|
| 4,830,006 A | 5/1989 | Haluska et al. | |
| 4,899,750 A | 2/1990 | Ekwall | |
| 4,949,720 A * | 8/1990 | Thompson | 607/11 |
| 5,201,865 A | 4/1993 | Kuehn | |
| 5,534,018 A | 7/1996 | Wahlstrand et al. | |
| 5,549,642 A | 8/1996 | Min et al. | |
| 5,755,742 A * | 5/1998 | Schuelke et al. | 607/27 |
| 5,824,016 A * | 10/1998 | Ekwall | 607/9 |
| 6,376,427 B1 * | 4/2002 | Mito | 504/137 |
| 6,788,972 B2 * | 9/2004 | Prutchi et al. | 607/28 |
| 6,801,806 B2 * | 10/2004 | Sun et al. | 607/14 |
| 7,050,851 B2 * | 5/2006 | Plombon et al. | 607/8 |
| 7,099,716 B1 * | 8/2006 | Levine | 607/28 |

FOREIGN PATENT DOCUMENTS

| | | |
|---|---|---|
| EP | 0715866 | 6/1996 |
| WO | WO 96/16694 | 6/1996 |
| WO | WO 96/37258 | 11/1996 |
| WO | WO 98/19738 | 5/1998 |

OTHER PUBLICATIONS

European Search Report, dated Jan. 28, 2008.

* cited by examiner

*Primary Examiner* — Niketa I Patel
*Assistant Examiner* — Hiba El-Kaissi
(74) *Attorney, Agent, or Firm* — Arc IP Law, PC; Joseph J. Mayo

(57) ABSTRACT

An implantable cardiac device includes a housing (2), pulse generator (7) therein to generate physiologically effective electrical pulses, a shock lead (3), externally of the housing (2), connectable to the pulse generator (7) and implantable into a patient's body to apply physiologically effective electrical pulses to the patient's body, a monitor (8) to automatically detect a lead condition as to whether the shock lead (3) is implanted or not, and control (9), which due to the detected lead condition automatically enables or disables the pulse generator (7).

11 Claims, 3 Drawing Sheets

IMPLANTABLE CARDIAC DEVICE WITH A SHOCK LEAD

BACKGROUND OF THE INVENTION

1. Field of the Invention

The invention refers to an implantable cardiac device comprising a housing, a pulse generator means therein to generate physiologically effective electrical pulses and a shock lead, externally of the housing, connectable to the pulse generator means and implantable into a patient's body to apply a physiologically effective electrical pulses to a patient's body.

2. Description of the Related Art

Implantable cardiac devices (ICDs), like defibrillators, apply high voltage shock pulses generated by pulse generator means within an ICD to the heart to terminate a patient's pathological state like a defibrillation. While handling an ICD during implantation or explantation, a user such as a physician or a nurse is in danger of receiving a high voltage shock which may be very hazardous to the user. The only protection against this risk is given by the master switch of the ICD, which manually deactivates shock deliveries during implantation, explantation or any other therapeutic or diagnostic procedures during which inappropriate shocks may occur. The problem is that a user might improperly handle the ICD during aforesaid procedures by for example not deactivating the pulse generator means via the master switch.

Although the aforesaid risks are minimized by the fact that ICDs are programmed at the producer to have the pulse generator means disabled, it is not uncommon however to "pre-program" an ICD before implanting it. Even when pre-programming is done, it would be unusual to enable shocks until the ICD has been implanted, nevertheless there remains a risk that a shock pulse is delivered inadvertently thereby subjecting the person handling the ICD to dangerous shock deliveries.

As noted above, some physicians will manually disable shock pulses during an implant procedure. A limitation of this method is that there is a risk that the physician may forget to re-enable shock capability at the end of the implant procedure. As a result, the patient may not be protected by the device until some future point in time when the programming error is discovered.

BRIEF SUMMARY OF THE INVENTION

Accordingly it is an object of the invention to provide an implantable cardiac device which avoids an inadvertent delivery of shock pulses during manually handling the ICD and the shock lead especially during implantation and explantation.

It is a further object of this invention to provide an automatic method to re-enable shock therapy at the end of an implant procedure and in this way ensure that shock therapy will be available to the patient when it is needed.

This object is achieved by an implantable cardiac device comprising a monitoring means to automatically detect a lead condition as to whether the shock lead is implanted or not and further comprising a control means which due to the detected lead condition automatically enables or disables the shock generator means.

Embodiments of the invention reliably prevent mistiming of shock pulses as the pulse generator means is automatically deactivated whenever the lead condition differs from the implanted state.

According to a preferred embodiment of the invention, as a parameter for the lead condition the monitoring means detects a voltage developing during a pace pulse or a low energy shock pulse applied by the pulse generator means via the shock lead. In the former case by measuring the voltage at the beginning and at the end of a pace pulse the shock lead impedance can be evaluated which again is an indicia of whether or not the shock lead is properly positioned in a patient's body. The impedance can be measured with pace pulses e.g. synchronous to ventricular paced or sensed cardiac events.

In the latter case again the impedance can be measured with sub 1 Joule shocks by detecting the time between the start of a test shock until the time, this test shock voltage has reached a level of 40% of the start voltage.

Another preferred embodiment of the invention provides an impedance measurement circuit for measuring the impedance of the shock lead as a parameter for the lead condition.

Further features and advantages of the invention are explained in the following description of at least one embodiment of the invention.

DETAILED DESCRIPTION

Figure 1:
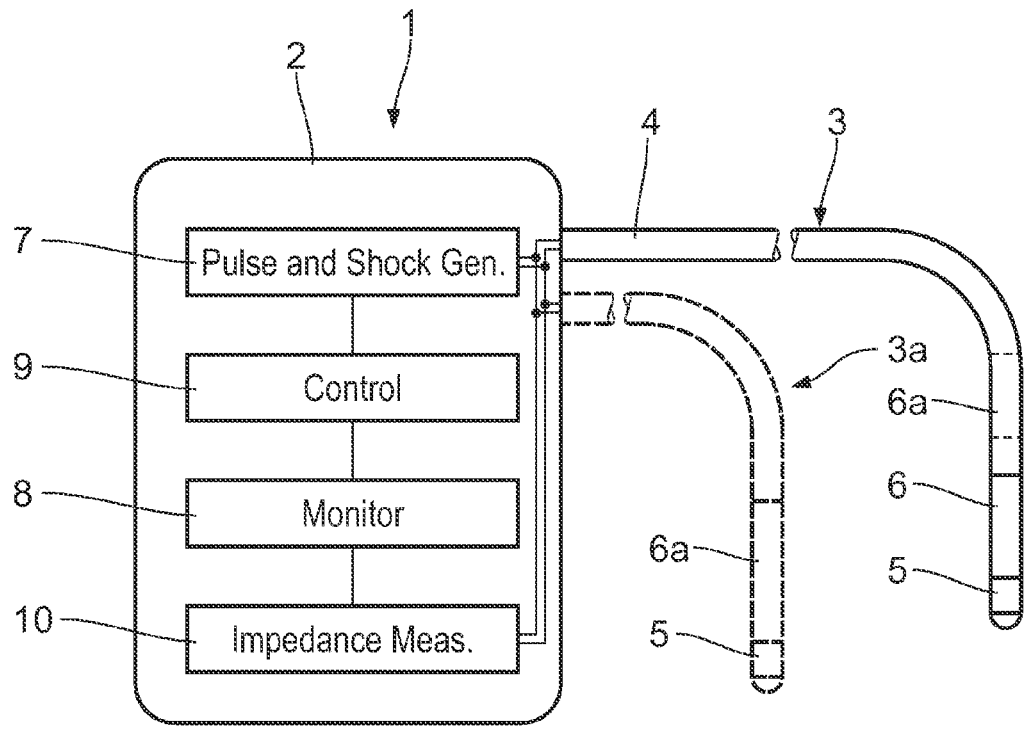
FIG. 1 shows a block diagram of an implantable cardiac device including a shock lead.

As is depicted in FIG. 1 the implantable cardiac device (ICD) 1 includes a housing 2 which is implantable e.g. subcutaneously into the thorax of a patient suffering from cardiac fibrillations. The ICD 1 is provided with an elongated shock lead 3 which is connected to the ICD with its proximal end 4 whereas the distal end 5 is lead into the body to supply the physiologically effective electrical pulses, i.e. for example high voltage shocks to the heart in case of fibrillations via shock electrodes 6 at the distal end 5.

The housing 2 accommodates as basic components a pulse and shock generator 7 to generate the cited physiologically effective electrical pulses, a monitor to automatically detect a lead condition as to whether the shock lead 3 is implanted or not, and a central control 9, preferably on the basis of a microprocessor, which amongst others automatically enables or disables the pulse and shock generator 7 depending on whether or not the monitor detects a properly implanted or explanted condition of the shock lead 3.

Alternatively, as is depicted with dashed lines in FIG. 1 two shock electrodes 6 and 6a are implanted either on the same shock lead 3 or on a second shock lead 3a. The monitor automatically detects a lead condition as to whether the shock lead 3 and 3a are implanted or not, and a central control 9, preferably on the basis of a microprocessor, which amongst others automatically enables or disables the pulse and shock generator 7 depending on whether or not the monitor detects a properly implanted or explanted condition of the shock lead 3 and lead 3a.

Figure 2:
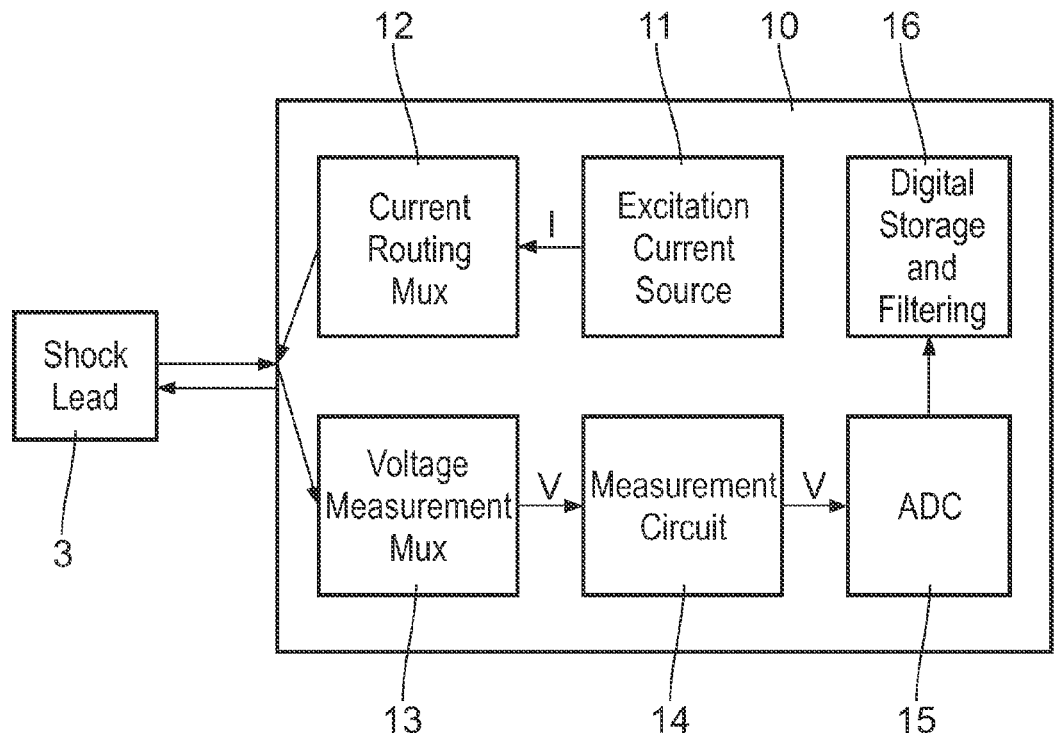
FIG. 2 shows a block diagram of an impedance measurement circuit.

Whereas the monitor 8 as a parameter for the lead condition might detect a voltage developing during a pace pulse also deliverable by the pulse and shock generator 7 or might detect the voltage drop of a low energy shock pulse of less than 1 Joule by the pulse and shock generator 7 it is preferred that the monitor 8 detects the lead condition with the help of an impedance measurement circuit 10 depicted in FIG. 1 and shown in more detail in FIG. 2. Tests have shown that the impedance of the shock lead 3 is a proper and reliable parameter for the detection whether or not the shock lead 3 is in a properly implanted or explanted condition. In case the shock lead 3 is properly implanted the lead impedance value is as a rule between 15 and 150 ohms. Thus when the monitor detects an impedance value by means of the impedance measurement circuit 10 which is within those limits the control enables the shock generator 7 as the shock lead 3 is detected to be properly implanted and thus shock pulses can be delivered without any danger for the physician.

Figure 3:
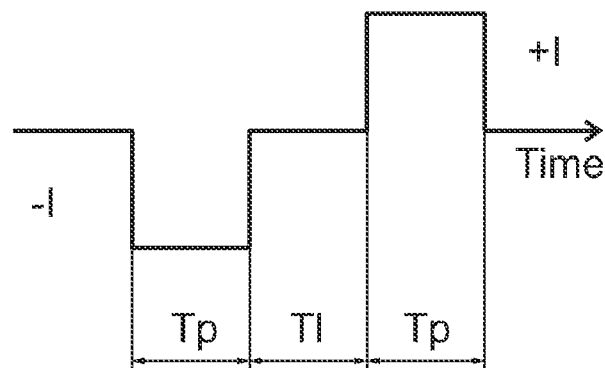
FIG. 3 shows a timing diagram of a biphasic measuring current.

As can be seen from FIG. 2 the impedance measurement circuit 10 includes an excitation current source 11, which generates a biphasic excitation current depicted in FIG. 3. The amplitude of the excitation current pulse is between 100 to 1000 μA+/−400 μA, the timing parameters are TI=15 μs and Tp=15 μs, 30 μs or 120 μs. A biphasic current pulse is selected to avoid polarization of the shock leads.

The excitation current I generated by the source 11 is delivered to a current routing multiplexer 12 which switches the excitation current pulses to the desired electrodes, e.g. the shock electrode 6 of the shock lead 3.

The voltage developing at the electrodes is taken up by the voltage measurement multiplexer 13 which passes on the measured voltage to the measurement circuit 14 which properly processes the voltage and passes an analogue value to the analogue digital converter 15 which converts the voltage into a digital value which is stored and filtered in the digital storage and filtering unit 16.

The aforesaid impedance measurement circuit 10 is basically known with implantable cardiac devices for other purposes. By means of the current routing mulitplexer 12 and the voltage measurement mulitplexer 13, however it is possible to also measure the shock lead impedance as a parameter for the lead condition. This measurement can be made relatively often, preferably with a period of detection between 1 second and 1 minute, because there is no noticeable indication to the patient that it is happening and the impact to longevity is minimal because of the small amount of current required. This makes it suitable for monitoring of the lead condition, specifically so that it can also detect short circuit or open circuit failures of the shock lead 3.

The control 9 can also be adapted to check the lead status before a shock is scheduled to be delivered. In case the lead impedance is measured to be very high, e.g. in a order of kOhms within some given time period and/or during a defined number (e.g. 2 to 5) of consecutive periods of detection the shock would be aborted by disabling the pulse generator 7. This control mechanism would also deactivate shocks in the ICD when it is to be explanted and the acting physician should forget to turn the ICD off by means of according programming.

Figure 4:
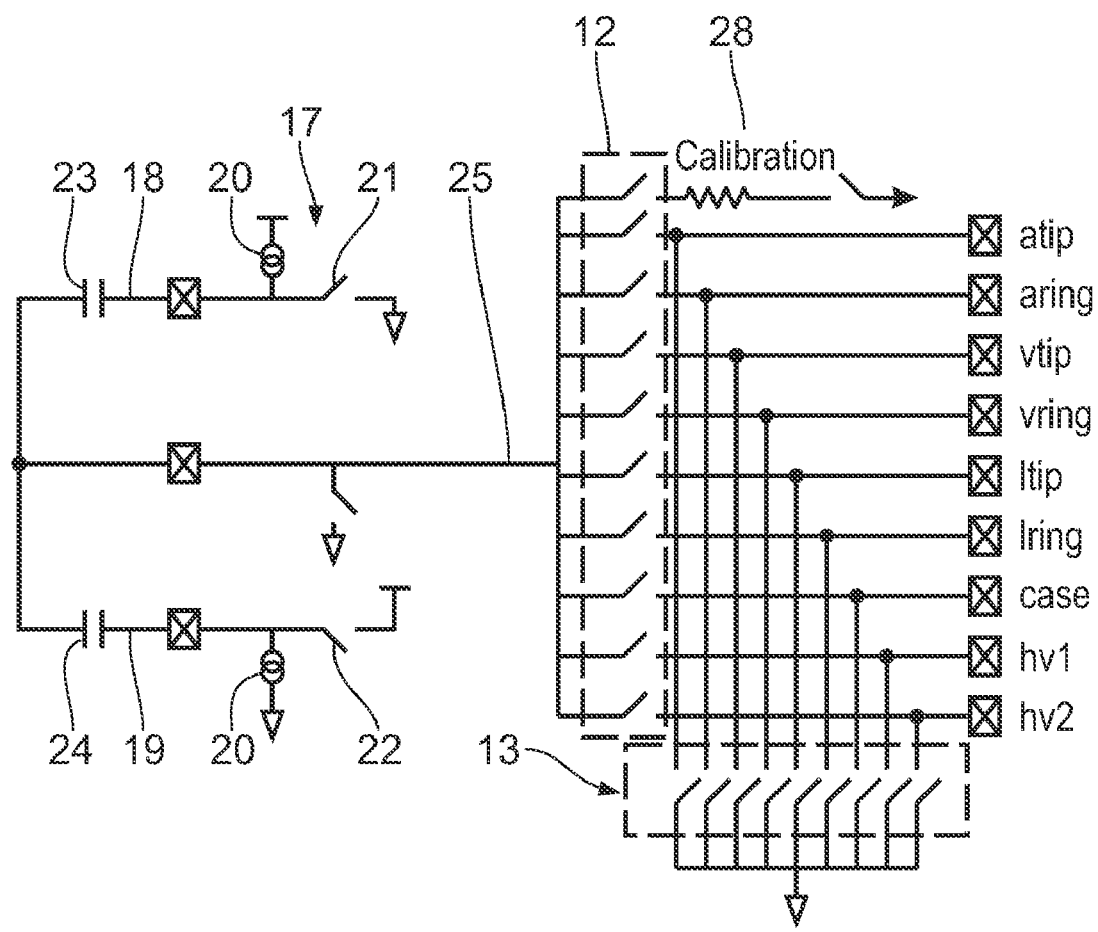
FIG. 4 shows a circuitry scheme of a current excitation circuit.

FIG. 4 shows the current excitation circuit 17 in the excitation current source 11 in which two branches 18, 19 are connected to the supply voltage 20. Switch elements 21, 22 connect the supply voltage 20 via capacitors 23, 24 alternately with the supply branch 25 which accordingly delivers current pulses shown in FIG. 3 to the current routing multiplexer 12. The amplitude of the excitation current is chosen to detect normal shock lead impedance between the above cited 15 and 150 ohms.

The circuitry of the current routing multiplexer 12 is controlled to supply the excitation current between connector "hv1" to connector "case" and between connector "hv2" to connector "case" thus subjecting the high voltage electrodes of the shock lead 3 and 3*b* with the excitation current.

The voltage developing at the shock lead electrodes due to the excitation current is measured via the voltage measurement multiplexer 13 depicted in FIG. 4 as can be explained in more detail in connection with FIG. 5.

In this drawing the connectors "case", "hv1" and "hv2" of the shock lead 3 are again shown. The shock electrodes are connected by closing the according switches for the connectors "hv1" for shock electrode 6 and "hv2" for shock electrode 6*a* versus "case". The according voltages are delivered via lines 26, 27 diagrammatically depicted as 26 in FIG. 5 to the measurement circuit 14. The impedance measurement amplifier values are chosen to detect normal shock lead impedance between 15 and 150 ohms.

Figure 5:
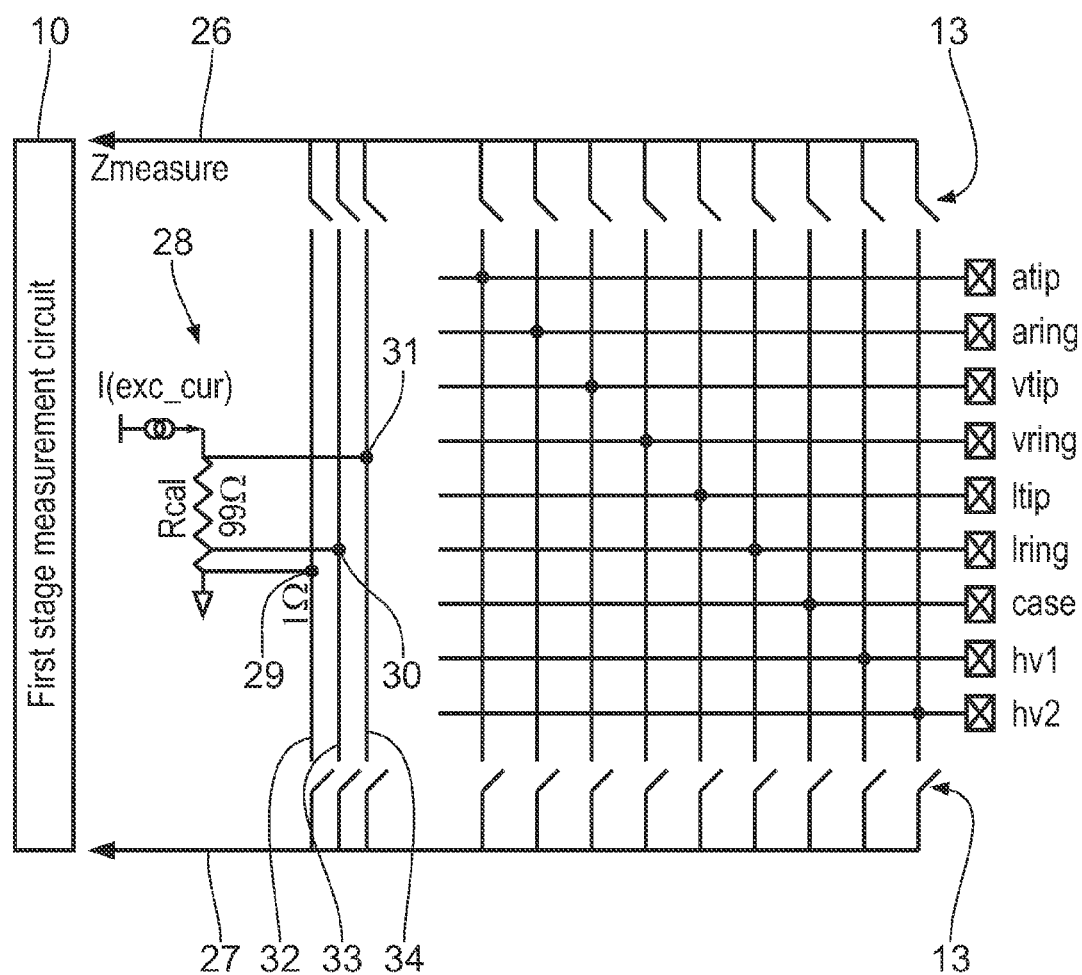
FIG. 5 shows a circuitry scheme of an impedance measurement circuit.

FIG. 5 further shows the calibration means 28 including a calibration resistor Rcal of about 100 Ohms connecting the supply voltage 20 to ground. The taps 29, 30, 31 of the calibration resistor Rcal are connected to according supply lines 32, 33, 34.

The connectors "atip", "aring", "vtip", "vring", "ltip" and "lring" shown in FIGS. 4 and 5 connect the usual sensing and pacing electrodes of a pacing lead with the ICD 1. As they are not relevant in connection with the present invention a detailed explanation is not necessary.

The following security algorithm is applied during detection of shock lead attachment (i.e. safe handling during implantation) and of shock lead detachment (i.e. safe handling during explantation):

The impedance measured at connector "hv1" to "case" and "hv2" to "case" is measured periodically between 1/second to 1/minute by alternating measurements.

No shock delivery is allowed unless the shock lead impedance of at least connector "hv1" or "hv2" is within 15 to 150 ohms for 2 to 5 consecutive measurements.

What is claimed is:
1. An implantable cardiac device comprising
a housing;
a pulse and shock generator situated within said housing and configured to generate physiologically effective electrical pulses or pace pulses;
at least one shock lead, external to said housing, connectable to said pulse generator and implantable into a patient's body to apply said physiologically effective electrical pulses to said patient's body;
a monitor to automatically detect a lead condition during a pace pulse selected from said pace pulses applied by said pulse and shock generator via said at least one shock lead as to whether said at least one shock lead is in an implanted state or in an explanted state;
wherein said lead condition is detected by said monitor with two voltage measurements associated with said pace pulse to determine a resistance comprising
a voltage measurement at a beginning of said pace pulse and
a voltage measurement at an end of said pace pulse; and,
a control, which due to a detected lead condition, automatically
enables said pulse and shock generator when all of said at least one shock lead is in said implanted state and disables said pulse and shock generator when any of said at least one shock lead is in said explanted state.
2. The implantable cardiac device according to claim 1, comprising an impedance measurement circuit associated with monitor configured to determine an impedance of said at least one shock lead from said measurements of the voltage at the beginning and the voltage at the end of said pace pulse as a parameter for said lead condition.

3. The implantable cardiac device according to claim 2, wherein an enabling impedance value for said parameter for said lead condition is between 15 and 150 Ohms.

4. The implantable cardiac device according to claim 1, wherein said monitor periodically detects said lead condition.

5. The implantable cardiac device according to claim 4, wherein said monitor periodically detects said lead condition using a period of detection between 1 second and 1 minute.

6. The implantable cardiac device according to claim 4, wherein an enabling impedance value between 15 and 150 Ohms is measured during a defined number of consecutive periods of detection.

7. The implantable cardiac device according to claim 4, wherein an enabling impedance value between 15 and 150 Ohms is measured in two possible shock configurations including hv1 to case, and hv2 to case, by alternating measurements during a defined number of consecutive periods of detection.

8. An implantable cardiac device comprising
   a housing;
   a pulse and shock generator situated within said housing and configured to generate physiologically effective electrical pulses that comprise low energy shock pulses or pace pulses;
   at least one shock lead, external to said housing, connectable to said pulse generator and implantable into a patient's body to apply said physiologically effective electrical pulses to said patient's body;
   a monitor to automatically detect a lead condition during a low energy shock pulse selected from said low energy shock pulses applied by said pulse and shock generator via said at least one shock lead as to whether said at least one shock lead is in an implanted state in an explanted implanted state;
   wherein said lead condition is detected by said monitor with detection of a time difference between a start time of the low energy shock pulse until a time that the low energy shock pulse has reached a predetermined voltage lower than a start voltage; and,
   a control which automatically
      enables said pulse and shock generator if the lead condition of all of said at least one shock lead is detected as said implanted state and
      disables said pulse and shock generator if the lead condition of any of said at least one shock lead is detected as said explanted state.

9. The implantable cardiac device according to claim 8, wherein said predetermined voltage lower than the start voltage is 40 percent of the start voltage.

10. The implantable cardiac device according to claim 8, wherein said monitor periodically detects said lead condition.

11. The implantable cardiac device according to claim 10, wherein said monitor periodically detects said lead condition with a period of detection between 1 second and 1 minute.

\* \* \* \* \*